United States Patent [19]

Villars

[11] Patent Number: 5,451,396
[45] Date of Patent: Sep. 19, 1995

[54] SHAVING COMPOSITIONS

[75] Inventor: William A. Villars, Racine, Wis.

[73] Assignee: S. C. Johnson & Son, Inc., Racine, Wis.

[21] Appl. No.: 153,862

[22] Filed: Nov. 17, 1993

[51] Int. Cl.$^6$ ............................................. A61K 7/15
[52] U.S. Cl. ..................... 424/73; 424/401; 514/944
[58] Field of Search ................................. 424/401, 73

[56] References Cited

U.S. PATENT DOCUMENTS

| | | | |
|---|---|---|---|
| 3,541,581 | 11/1970 | Monson | 252/90 |
| 4,917,884 | 4/1990 | Roberts | 424/73 |
| 4,963,352 | 10/1990 | Roberts | 424/73 |
| 5,262,154 | 11/1993 | Wendel et al. | 424/73 |

*Primary Examiner*—Thurman K. Page
*Assistant Examiner*—James M. Spear
*Attorney, Agent, or Firm*—Laura L. Bozek; J. William Frank, III

[57] ABSTRACT

The present invention provides post-foaming shave gels having improved clarity and gel tine strength by the addition of effective amounts of benzyl alcohol, or a mixture of benzyl alcohol and lauryl alcohol to the compositions at a pH of at least 8. These post-foaming gels maintain their strength and clarity for at least 180 days. The present invention also provides shaving foam compositions which may be produced from high performance post-foaming shaving gel by the addition of from about 1.0% to about 15% by weight of benzyl alcohol to the compositions without significantly altering the propellant system or otherwise changing the formulation or aerosol gel can type. Traditional shave foam cans with dip tubes can also be used for the foam product. These shaving compositions may be produced and packaged by current commercial methods.

5 Claims, No Drawings

SHAVING COMPOSITIONS

TECHNICAL FIELD

This invention relates to novel shaving compositions. The post-foaming shave gel compositions of the present invention retain their clarity and gel tine strength for at least 180 days. The shaving foam compositions of the present invention may be produced from post-foaming gel compositions without changing the propellant system.

BACKGROUND ART

Clear post-foaming gels are known in the industry. For example, U.S. Pat. No. 3,541,581 to Monson discloses clear, water-based post-foaming gel compositions comprising water-soluble soap, gelling aid such as cellulose, a post-foaming agent and miscellaneous additives.

However, clearer, strong gels are desired in the shaving product industry because of their appearance when dispensed and an improved adherence to the skin while shaving especially in shower environments.

Clear products are also becoming increasingly more desirable to consumers because of growing awareness that skin irritation may be caused by certain dyes and other colorants. Clear gels appear less irritating to consumers. This is especially important to physicians such as dermatologists who worry about worsening skin conditions.

It is also desired in the shaving product industry to produce a shave foam having the shaving performance of a post-foaming shave gel. Post-foaming shave gels out perform shaving creams (e.g., fewer nicks and cuts, and less skin irritation and razor burn). Currently, post-foaming shave gels may be converted into foam by diluting the formula to make it more fluid (e.g., addition of 25% more water) and using a traditional foam aerosol container, or alternatively, by significantly increasing the amount of propellant used. However, these methods generally result in lowering the shave performance of the compositions.

Another technique for converting gel to foam requires the substitution of the post-foaming agent with a higher pressure propellant. The higher pressure propellant causes the gel to bubble more quickly when dispensed from a gel container with a foam valve and actuator. However, using multiple propellant systems for gels and foams is not desirable because of increased manufacturing costs due to the necessity of maintaining and switching propellant systems. In addition, higher pressure propellants are sometimes more difficult to utilize in production.

Therefore, it is an object of the present invention to provide a post-foaming gel with improved clarity and strength which remains clear for at least 180 days.

It is a further object of this invention to provide a post-foaming gel composition which is soothing to the skin of the user.

It is an additional object of the present invention to provide a shaving foam which does not require the substitution of different propellants or significant changes in other ingredients of post-foaming shave gel compositions to achieve a shaving foam which may be used in shave gel containers with modification of the valve and actuator or in traditional shave foam aerosol dispensers.

The pH of the post-foaming gel compositions of the present invention is at least 8.

SUMMARY OF THE INVENTION

In a broad embodiment of the present invention, these objects and others are provided in an improved shaving compositions which comprise an effective amount of a water-soluble soap, a post-foaming agent, a gelling agent and an effective amount of benzyl alcohol in a water base, wherein the composition has a pH of at least 8. The present invention is based upon the finding that the formulations of the invention provide clear gels which retain their shaving properties and are particularly suited to packaging in conventional post-foaming shaving gel dispensing containers.

The present invention is also based upon the finding that shaving foams may be produced from higher performing post-foaming shave gels by the addition of an effective amount of benzyl alcohol which may be packaged in conventional aerosol dispensing containers used for shave gels or shave foams.

DETAILED DESCRIPTION OF THE INVENTION

Benzyl alcohol, in extremely minor quantities is well known by those of ordinary skill as a preservative for shaving compositions. Benzyl alcohol is also used in non-aerosol shaving compositions to purportedly facilitate penetration of shaving compositions into the hair.

For example, U.S. Pat. Nos. 4,917,884 and 4,963,352 to Roberts, disclose low-foaming, clear shaving compositions containing glyoxal, urea and alkanolamine/fatty acid soap at a pH of below 7.0. Optionally, 0.1% to 4.0%, preferably from about 0.1% to about 2.0% by weight of benzyl alcohol may be added to the acidic non-aerosol shaving compositions. The compositions of the '884 and '352 patents do not disclose or teach one of ordinary skill how to produce clearer, stronger post-foaming shave gels. These patents also do not disclose or teach the production of stable shaving foam products without changing the other components of the post-foaming shave gel compositions.

It is surprising that the addition of about 0.5% to about 1.0% by weight of benzyl alcohol either alone, or in combination with 1-dodecanol, commonly known as lauryl alcohol, can provide clearer, stronger post-foaming shave gels. The addition of benzyl alcohol also provides soothing properties to the skin, which is beneficial when shaving in sensitive parts of the body such as under arms.

It is equally surprising that stable shaving foam compositions may also be produced from post-foaming shave gels by the addition of over 1.0% to about 15% by weight of benzyl alcohol without changing propellants or significantly altering other ingredients found in high-performance post-foaming shave gels.

The present invention allows the addition of small amounts of benzyl alcohol to high-performing post-foaming shave gel to adequately thin the gel to achieve an instant shave foam having better shave-performance than conventional shave foams without altering the propellant system. Thus benzyl alcohol allows the use of current gel aerosol type shave dispensers by merely changing the valve and/or actuator, or the use of traditional shave foam aerosol can having a dip tube.

The water soluble soaps used in accordance with the present invention are well known in the art and may be prepared in any conventional manner such as the Monson technique. Preferably, the water-soluble soap is a water-soluble salt of a higher fatty acid. Such soaps are well known in the art and may be purchased or prepared in any conventional manner. For example, these soaps may be prepared by reacting a basic material such as triethanolamine directly with a fatty acid such as a saturated or unsaturated fatty acid which is $C_{10}$ to $C_{22}$. Preferred soaps include the water-soluble stearate and palmitate soaps, such as the soluble amine salts of stearic and palmitic acid. The triethanolamine soaps of these acids are especially preferred. The soaps of this invention are preferably employed in amounts from about 5% to about 20% by weight of the total composition.

It is well known that the commercial product known as stearic acid is actually a mixture consisting primarily of stearic and palmitic acids. Therefore, the term "stearates" is used herein to designate soaps of commercial stearic acid, although soaps of chemically pure stearic or palmitic acid work equally well for the purposes of this invention. Preferably, palmitic acid available under the trademark "Emersol" is used in the present invention. Most preferably, the palmitic acid used is sold under the trademark "Emersol-140 (3:1)" which is a blend of palmitic acid and stearic acid in a 3:1 ratio.

The preferred gelling aids, found to be most suitable for use in the present invention, are water-soluble hydroxyalkyl cellulose or naturally derived gums such as xanthan, various synthesized polymers such as polyvinyl pyrrolidone, as well as chemically or enzymatically modified derivatives of these materials. These materials contribute sufficient viscosity to provide the desired levels of lubricity and stability to the product. Hydroxyalkyl cellulose thickeners may be commonly produced by combining an alkyl cellulose and an alkylene oxide such as ethylene or propylene oxide. Products of this type are marketed under the trademarks "Natrosol" and "Klucel" and are available in a variety of viscosity grades. One such preferred grade of hydroxyalkyl cellulose is the hydroxyethyl cellulose sold under the trademark "Natrosol 250 HHR". Care must be taken when using these gelling aids since they may decrease the clarity of post-foaming gels and/or reduce the shave performance of the compositions.

The exact amount of gelling aid used in the practice of this invention will depend to some extent upon the viscosity grade employed, but will generally be on the order of about 0.1% to about 5.0% by weight of the total composition. Mixtures of two or more gelling aids can be employed. An advantage of using benzyl alcohol to alter the viscosity of post-foaming gels is that gelling aids such as hydroxyalkyl cellulose tend to make shave gels cloudy or hazy.

The post-foaming agents or propellants of the present invention are liquids or are liquifiable and include saturated aliphatic hydrocarbons having from 4 to 6 carbon atoms, including butanes, such as n-butane or isobutane; pentanes such as n-pentane or isopentane; and hexane. Mixtures of hydrocarbon post-foaming agents may be especially useful for providing the particular vapor pressure desired. An advantage of using mixtures of two or more post-foaming agents is that it permits a precise, accurate adjustment of the vapor pressure of the gel to achieve the desired foaming qualities. The addition of the hydrocarbon post-foaming agent to the premixed blend of the other ingredients changes the cloudy soap intermediate to a clear gel and also increases the viscosity of the product. The clarity of this gel is further enhanced by the addition of benzyl alcohol.

The concentration of the post-foaming agent in the gel is preferably from about 0.5 to about 10% by weight of the total composition. Substantially smaller amounts of post-foaming agent will fail to provide the desirable foaming and lathering characteristics. Significantly larger amounts may cause premature foaming of the composition as it is being expelled from the container. The quality of this expelled foam is often poor due to the dilution of the gel by the post-foaming agents. The use of benzyl alcohol reduces the need for additional propellants thus maintaining a higher concentration of shave performance enhancing ingredients. This allows for better performing shaving foam compositions.

In post-foaming shaving gels of the present invention, benzyl alcohol is typically present in an amount from about 0.1% to about 1.0%, preferably 0.5% to about 1.0%, and most preferably 0.5% by weight of the total compositions for clarification and strengthening purposes. In shaving foam compositions of the present invention, benzyl alcohol is present in amounts from about 1.0% to about 15%, preferably about 3.0% to about 4.0% by weight of the total shaving composition.

In a preferred embodiment, about 0.5% by weight of lauryl alcohol is added to the post-foaming shaving gel compositions of the present invention to further enhance the clarity of the gel.

Adjuvant materials are compatible with these formulations. Examples of adjuvant materials include, but are not limited to, Vitamin E, fatty alcohols, aliphatic fatty acid esters, lanolin, lanolin alcohols, glycerides, mineral oil, and many others. Coloring agents, dyes, perfumes, fragrance oils and odor masking compounds such as "pentadecalactone" available from Firmetech may also be added. The glycerides are preferably distilled monoglycerides such as those available under the trademarks "Myverol", by Eastman Chemical Products. One preferred grade of distilled monoglycerides is sold under the trademark "Myverol 18-92".

As indicated above, the addition of various adjuvant materials to the stable gel is contemplated by the present invention. Thus, the finished commercial compositions will ordinarily contain materials such as, but not limited to, dyes, anti-oxidants such as BHT, humectants, natural oils, esters, glycerin, lanolin, aloe, lecithin, fatty alcohols, OTC Monograph active materials, nonionic surfactants, amphoterics, polymers, insoluble particulates, or other materials which provide additional particularly desired properties.

Vitamin E or dl-alpha tocopheryl acetate is sold under the trademark "Vitamin E Acetate" by Hoffman LaRoche, Inc. The moisturizing agent or lubricant is preferably "Sorbitol", more preferably, "Sorbitol, 70%, U.S.P.".

The following examples are illustrative of compositions falling with the general scope of the invention. The following compositions were prepared and evaluated as shaving preparations. All amounts are given in parts by weight unless indicated otherwise.

EXAMPLE I

In order to prepare a series of post-foaming gels within the scope of the present invention, a base gel formula was employed which may be made by the following procedures:

|  | % w/w |
|---|---|
| Deionized Water | q.s. |

| | % w/w |
|---|---|
| Natrosol 250 HHR | 0.41 |
| Sorbitol, 70% Solution | 1.78 |
| Triethanolamine, 85% | 6.36 |
| Vitamin E Acetate | 0.10 |
| Emersol 140 (3:1 Palmitic acid/Stearic acid blend) | 11.09 |
| Myverol 18-92 (distilled monoglycerides) | 1.66 |
| BHT | 0.03 |
| Pentadecalactone | 0.05 |

A fatty acid and an alkanolamide of the invention are mixed and preheated to 180° F. The Natrosol and any desired colorants are blended together into 60° F. water. The water mixture is heated to 180° F. and the amine is added. The amide acid mixture at 180° F. is added to the water mixture at 180° F. with agitation. After mixing, the resulting mixture is cooled to 160° F. At this point, other desired additives are introduced. Solid additive materials are warmed to 140° F. before being added to the mixture. The mixture is then cooled to 100° F. and any desired perfumes are added.

After any necessary mixing is completed, the mixture is further cooled to 40° F. This mixture is then mixed with the particular hydrocarbon blend and filled into an aerosol dispenser within the mixture is separated from the propellant such as by a collapsible bag or diaphragm such as that described in U.S. Pat. 3,541,581.

The gel clarity and strength of the post-foaming gels of the present invention at a room temperature of approximately 72° F. may be determined as follows:

Gel clarity may be determined by filling a 2.5 cc disposable syringe with the finished product directly from the can and by visually assigning a clarity number which correlates to the appearance of the markings on the syringe, as described in Table B.

| Number | Description | Property |
|---|---|---|
| 5 | Clear | Transparent |
| 4 | Semi-Clear | Easily Read |
| 3 | Translucent | Fuzzy |
| 2 | Hazy | Barely Discernible |
| 1 | Cloudy | Unable to See Markings |

Clarity was assessed by dispensing a can of material into a flow cell mounted in a spectrophotometer. If a dye or other inert ingredients was present that could interfere with clarity measurements, a wave length was chosen where dye absorbency was low, such as 530 nm. The percent transmittance of various formulations which were measured at that wave length by this method correlates well to the simple visual evaluation described above.

Gel strength was assessed by use of the tine test in which metal rods were arranged horizontally in comb fashion such that each pair of rods was separated by an increasingly larger distance. The rods thereby form a grid onto which finished products are actuated. A stronger gel would naturally span a larger number of tines.

In order to assess the gel strength and clarity of post-foaming gel compositions of this invention, 6 formulations were prepared in accordance with the procedure of Example I. The formulations were identical in constituents and amounts to the base gel formulation of Example I except that the benzyl alcohol and lauryl alcohol were added to the water mixture before the addition of the amine in the following amounts:

| | % Benzyl Alcohol | % 1-Dodecanol | % Clarity | | Gel Time Strength |
|---|---|---|---|---|---|
| | | | Initial | Average of Initial 1,2 & 6 | |
| 1. | 0 | 0 | 49.0 | 55.3 | 42.5 |
| 2. | 0.5 | 0 | 93.0 | 86.5 | 45.5 |
| 3. | 1.0 | 0 | 81.0 | 78.5 | 45.5 |
| 4. | 3.0 | 0 | 0.9 | 0.7 | 1.0 |
| 5. | 4.0 | 0 | — | | 0.0 |
| 6. | 0.5 | 0.5 | 96.0 | 88.0 | — |

The above values for clarity reflect the initial gel clarity ("Initial") as well as the clarity of the gel stored at room temperature averaged over a 6 month time period. As shown by the above chart, post-foaming gels containing benzyl alcohol or a combination of benzyl alcohol and lauryl alcohol are clearer and stronger, up to 6 months storage at room temperature, than the basic gel formula.

INDUSTRIAL APPLICABILITY

In practice the clearer and stronger post-foaming shave gel compositions of the present invention may be produced by typical commercial methods and packaged in conventional shave gel dispensers. This avoids the need to make expensive and time-consuming changes in current manufacturing and packaging operations. In addition, the shave foam compositions of the present invention may be produced from post-foaming shave gels without the need for significantly changing current manufacturing lines or aerosol canisters.

It should be understood that various modifications can be made to the preferred embodiments disclosed herein without departing from the spirit and scope of the invention, or the loss of intended advantages. Thus, other examples applying the principles described herein are entitled to fall within the scope of the invention, provided that the features stated in any of the following claims, or the equivalent of such the employed.

I claim:

1. In an aqueous post-foaming gel composition which comprises effective amounts of a water-soluble soap, a volatile post-foaming agent, and water to result in an aqueous post-foaming gel composition, the improvement which comprises employing an effective amount of benzyl alcohol, wherein the amount of the benzyl alcohol present in the composition is such that it enhances the clarity and gel strength of the post-foaming gel composition for at least 180 days, and the pH of the composition is at least 8.

2. The gel composition as claimed in claim 1, wherein the effective amount of benzyl alcohol is about 0.5 to about 1.0% by wt. of the total gel composition.

3. A stable post-foaming gel composition, comprising:
   60-90% water, by weight of the total gel composition;
   5-20% by weight of water-soluble soap;
   0.5-10% by weight of a volatile post-foaming agent selected from the group consisting of saturated aliphatic hydrocarbons and mixtures thereof;
   0.1-4% by weight of at least one water-soluble polymer gelling aid;
   about 0.5% to about 1.0% by weight of benzyl alcohol; and
   about 0.5% by weight of 1-dodecanol, wherein the pH of the composition is at least 8.

4. A shaving foam composition, comprising an effective amount of a water-soluble soap; an effective amount of gelling aid an effective amount of a post-foaming agent and about 1.0% to about 15% by weight of benzyl alcohol, wherein the pH of the composition is at least 8.

5. A shaving foam composition as claimed in claim 4, wherein the amount of benzyl alcohol is from about 3.0% to about 4.0% by weight of the total composition.

* * * * *

UNITED STATES PATENT AND TRADEMARK OFFICE
CERTIFICATE OF CORRECTION

Patent No.   : 5,451,396
Dated        : Sept. 19, 1995
Inventor     : William A. Villars It is certified that errors appear in the above-identified patent and that said Letters Patent is hereby corrected as shown below:

Column 2, line 32, please delete "glyoxal", and insert --glycoxal--.

Column 6, the last subheading in the table, delete "Gel Time", and insert --Gel Tine--.

<u>In Claims</u>:

Claim 4, line 3, after "gelling aid," please insert --;--.

Signed and Sealed this

Tenth Day of April, 2001

Attest:

NICHOLAS P. GODICI

*Attesting Officer*   *Acting Director of the United States Patent and Trademark Office*